(12) United States Patent
Haack et al.

(10) Patent No.: US 9,278,349 B2
(45) Date of Patent: Mar. 8, 2016

(54) PIPETTING DEVICE, MODULAR PIPETTING UNIT, PIPETTING SYSTEM AND METHOD FOR PIPETTING OF FLUID SAMPLES

(71) Applicant: Roche Molecular Systems, Inc., Pleasanton, CA (US)

(72) Inventors: Carsten Haack, Huenenberg See (CH); Thomas Engel, Buonas (CH); Tobias Holenstein, Kuessnacht am Rigi (CH)

(73) Assignee: Roche Molecular Systems, Inc., Pleasanton, CA (US)

( * ) Notice: Subject to any disclaimer, the term of this patent is extended or adjusted under 35 U.S.C. 154(b) by 0 days.

(21) Appl. No.: 14/528,182

(22) Filed: Oct. 30, 2014

(65) Prior Publication Data

US 2015/0056111 A1    Feb. 26, 2015

Related U.S. Application Data

(63) Continuation of application No. 12/623,785, filed on Nov. 23, 2009, now Pat. No. 8,900,878.

(30) Foreign Application Priority Data

Nov. 28, 2008  (EP) .................................... 08170321

(51) Int. Cl.
*B01L 3/02* (2006.01)
*G01N 35/00* (2006.01)
*G01N 35/10* (2006.01)

(52) U.S. Cl.
CPC ............ *B01L 3/021* (2013.01); *G01N 35/1072* (2013.01); *B01L 2400/0475* (2013.01); *G01N 35/0099* (2013.01); *G01N 35/1011* (2013.01); *Y10T 436/119163* (2015.01); *Y10T 436/2575* (2015.01)

(58) Field of Classification Search
CPC .............. G01N 35/10; G01N 35/1002; G01N 35/1009; G01N 2035/1025
USPC ......... 422/500–501, 504, 509, 511, 518, 521, 422/62–68.1; 436/54, 180; 73/863.32, 864, 73/864.01

See application file for complete search history.

(56) References Cited

U.S. PATENT DOCUMENTS 3,963,148 A * 6/1976 Proni et al. .................... 222/132
4,140,020 A * 2/1979 Cook ......................... 73/864.12
(Continued)

FOREIGN PATENT DOCUMENTS

EP    1557675 A2    7/2005
EP    1669762 A1    6/2006
(Continued)

*Primary Examiner* — Brian R Gordon
(74) *Attorney, Agent, or Firm* — M. Reza Savari (57) ABSTRACT

A pipetting device having a modular pipetting unit including a pipetting tip for pipetting of fluid samples and a pump conduit for transferring a negative or positive pressure to the pipetting tip is disclosed. The pipetting tip and a portion of the pump conduit adjoining the pipetting tip mutually define a fluid sample conduit for receiving the fluid samples. The modular pipetting unit is detachably attached to an automated positioning device for positioning the modular pipetting unit. A system and method for pipetting of fluid samples using such a pipetting device are also disclosed wherein pipetting of the fluid samples is performed in such a manner that each pipetted fluid sample volume is smaller than a volume of the fluid sample conduit.

15 Claims, 5 Drawing Sheets

(56) References Cited

U.S. PATENT DOCUMENTS

| | | | |
|---|---|---|---|
| 4,788,150 A * | 11/1988 | Nelson et al. | 436/45 |
| 4,856,073 A * | 8/1989 | Farber et al. | 382/128 |
| 6,361,289 B1 | 3/2002 | Hennes et al. | |
| 6,902,703 B2 | 6/2005 | Marquiss et al. | |
| 7,160,511 B2 | 1/2007 | Takahashi et al. | |
| 7,244,396 B2 | 7/2007 | Chait et al. | |
| 7,541,001 B2 | 6/2009 | Kraemer et al. | |
| 7,575,718 B2 | 8/2009 | Shimizu | |
| 7,850,912 B2 | 12/2010 | Favuzzi et al. | |
| 7,875,245 B2 | 1/2011 | Favuzzi et al. | |
| 7,964,160 B2 | 6/2011 | Zuppiger et al. | |
| 7,972,576 B2 * | 7/2011 | Langer et al. | 422/501 |
| 8,012,767 B2 * | 9/2011 | Rasnow et al. | 436/180 |
| 2002/0064482 A1 | 5/2002 | Tisone et al. | |
| 2004/0050866 A1 | 3/2004 | Ingenhoven et al. | |
| 2006/0105359 A1 | 5/2006 | Favuzzi et al. | |
| 2007/0031294 A1 | 2/2007 | Gaillard et al. | |
| 2008/0019878 A1 | 1/2008 | Trump | |
| 2009/0155123 A1 | 6/2009 | Williams et al. | |

FOREIGN PATENT DOCUMENTS

| | | |
|---|---|---|
| EP | 1712285 A1 | 10/2006 |
| WO | 2005120710 A2 | 12/2005 |
| WO | 2007045341 A2 | 4/2007 |

* cited by examiner

PIPETTING DEVICE, MODULAR PIPETTING UNIT, PIPETTING SYSTEM AND METHOD FOR PIPETTING OF FLUID SAMPLES

CROSS-REFERENCES TO RELATED APPLICATIONS

This application is a continuation of application Ser. No. 12/623,785, filed Nov. 23, 2009, which claims the benefit of priority from EP08170321.7 filed Nov. 28, 2008, the contents of which are incorporated by reference herein in their entirety.

TECHNICAL FIELD

Embodiments of the present invention relate generally to automated handling of fluid samples and more particularly to a pipetting device, a modular pipetting unit, a pipetting system and a method for the automated pipetting of fluid samples.

BACKGROUND

In consideration of the fact that there is an ongoing increase in (bio-)chemical and genetic analyses and assays, a strong demand for the automated pipetting of fluids can be observed.

In recent years, many efforts have been made to develop new automated pipetting devices most often provided with a plurality of pipettes enabling plural pipetting operations in parallel. Each of the pipettes is provided with a pipetting tip connected to a pump by means of a pump conduit to transfer pump-generated negative or positive pressure to the pipetting tip for aspirating and dispensing of fluids, respectively. Conventionally, plunger pumps are being used for pipetting operations which advantageously allow for high-precision pipetting of fluids, however, typically are heavy in weight and thus may not be moved together with the pipetting tips due to an undesired strong increase in inertia. This especially applies to the case of independently operable pipettes requiring each pipette to be provided with a separate plunger pump.

Hence, plunger pumps are kept stationary when moving the pipetting tips and, for instance, are fixed to a base-plate, which, however, enlarges the overall dimensions of the automated pipetting device and hinders an integrated and compact design of the pipettes. Moreover, lengthy pump conduits in-between pump and pipetting tips aggravate various maintenance tasks (e.g. leakage detection) and disadvantageously enlarge dead volumes which, however, essentially influence precision of pipetting operations.

US-patent application No. 2008/0019878 A1 to Trump discloses a positioning device for pipettes in which a profiled rail accommodates a pump drive. While such positioning device makes the pump drive an integrated part of the profiled rail, such construction, however, disadvantageously requires the positioning device to be newly adjusted each time the pump drive has to be serviced. For that reason, maintenance of the pump drive due to failures will result in undesirably high costs. Furthermore, irrespective of the fact that plural pipettes require a rather complex construction, the positioning device may not be readily adapted to varying demands.

SUMMARY

It is against the above background that that present invention in one embodiment relates to a pipetting device that is flexible in use and allows for an integrated and compact design of independent pipettes. The pipetting device comprises at least one modular pipetting unit which includes a pipetting tip for pipetting of fluid samples and a pump conduit for transferring a negative or positive pressure to the pipetting tip, wherein the pipetting tip and at least a portion of the pump conduit adjoining the pipetting tip mutually define a fluid sample conduit for receiving the fluid samples, and wherein the modular pipetting unit being detachably attached to an automated positioning device for positioning the modular pipetting unit. The present invention in other embodiments relates to such a modular pipetting unit and a method for pipetting of fluid samples using such a pipetting device are also disclosed. The pipetting of the fluid samples is performed in such that each pipetted fluid sample volume is smaller than a volume of the fluid sample conduit. The present invention in a further embodiment relates to a pipetting system, comprising at least one pipetting unit including a pipetting tip for pipetting fluid samples and a pump conduit for transferring a negative or positive pressure to the pipetting tip, wherein the pipetting tip and at least a portion of the pump conduit adjoining the pipetting tip mutually define a fluid sample conduit for receiving the fluid samples; an automated positioning device for positioning of the at least one pipetting unit; and a controller for controlling of pipetting of the fluid samples, configured to control pipetting of fluids such that each pipetted volume of the fluid samples is smaller than a volume of the fluid sample conduit.

In one preferred embodiment, a pipetting device is disclosed and comprises an automated positioning device; and at least one modular pipetting unit which includes a pipetting tip for pipetting of fluid samples and a pump conduit for transferring a negative or positive pressure to the pipetting tip. The pipetting tip and at least a portion of the pump conduit adjoining the pipetting tip mutually define a fluid sample conduit receiving the fluid samples. The modular pipetting unit is detachably attached to the automated positioning device which positions the modular pipetting unit.

In another preferred embodiment, a modular pipetting unit is disclosed and comprises at least one pipetting tip for pipetting of fluid samples; and a pump conduit for transferring a negative or positive pressure to the pipetting tip. The pipetting tip and at least a portion of the pump conduit adjoining the pipetting tip mutually define a fluid sample conduit for accommodating the fluid samples.

In still another preferred embodiment, a method for pipetting of fluid samples is disclosed. The method comprises providing a pipetting device which comprises at least one pipetting unit provided with a pipetting tip for pipetting of fluid samples and a pump conduit, the pipetting tip and at least a portion of the pump conduit adjoining the pipetting tip mutually define a fluid sample conduit, and the pump conduit being at least partly filled with a liquid system fluid; and moving the liquid system fluid in the pump conduit to transfer a negative or positive pressure to the pipetting tip via the fluid sample conduit to pipette the fluid samples, wherein a pipetted fluid sample volume is smaller than a volume of the fluid sample conduit.

In yet another preferred embodiment, a pipetting system is disclosed and comprises at least one pipetting unit which includes a pipetting tip for pipetting fluid samples and a pump conduit for transferring a negative or positive pressure to the pipetting tip, wherein the pipetting tip and at least a portion of the pump conduit adjoining the pipetting tip mutually define a fluid sample conduit for receiving the fluid samples; an automated positioning device for positioning of the at least one pipetting unit; and a controller for controlling pipetting of the fluid samples such that each pipetted volume of the fluid samples is smaller than a volume of the fluid sample conduit.

Other and further embodiments, features and advantages of the invention will appear more fully from the accompanying drawings, the following detailed description, and the appended claims.

BRIEF DESCRIPTION OF THE DRAWINGS

In the drawings like designations denote like or similar elements, and in which.

REFERENCE LIST

1 Pipetting device
2 Pipetting module
3 Pipetting tip
4 Pump conduit
5 First portion of pump conduit
6 Guiding face
7 Cartridge
8 Inner wall
9 Outer surface
10 Fluidic connector
11 First curved tubing portion
12 Cavity
13 Sensor arrangement
14 Electric connector
15 transfer head
16 Horizontal guiding rail
17 Guiding chain
18 Gearwheel pump
19 Vertical guiding rail
20 Sliding carriage
21 Chain link
22 Longer tubing portion
23 Shorter tubing portion
24 Curved tubing portion
25 Fluid sample conduit
26 Positioning device
27 Pipetting channel
28 Optical flow sensor
29 Reservoir tubing
30 Pressure sensor
31 System fluid valve
32 System fluid reservoir
33 DC electric motor
34 First inlet/outlet port
35 Second inlet/outlet port
36 Inner rotor
37 Outer rotor
38 Inner rotor rotation axis
39 Outer rotor rotation axis
40 Pressure chamber
41 Controller

DETAILED DESCRIPTION

According to an embodiment of the invention, a pipetting device for pipetting of fluid samples is provided. The pipetting device comprises at least one modular pipetting unit, in the following referred to as "pipetting module", including a pipetting tip for aspirating and dispensing (i.e. pipetting) of fluids and a pump conduit for transferring a pump-generated negative or positive pressure to the pipetting tip. The pipetting tip and at least a portion of the pump conduit adjoining the pipetting tip mutually define a duct, in the following referred to as "fluid sample conduit", which is used for receiving fluids aspirated through the pipetting tip. The pump conduit may, e.g., be embodied as wound (e.g. flexible) entity including one or more windings. Such pump conduit allows for a wide range of volumes be pipetted according to the specific demands of the user. Moreover, the pump conduit can be readily replaced in particular in case of contamination of the pump conduit. Each winding may, e.g., include linearly extending portions connected by curved portions. Specifically, the pump conduit may include plural windings, each of which including linearly extending portions connected by curved portions, wherein the pipetting tip is being connected to a linearly extending portion, i.e. end portion of the pump conduit. In the latter case, the fluid sample conduit may, e.g., be composed of the pipetting tip and the linearly extending portion immediately connected therewith. The pipetting device further includes an automated positioning device for positioning of the at least one pipetting module with the pipetting module being detachably attached to the automated positioning device. Accordingly, the pipetting module is being configured as a detachably mounted structural entity which can be fixed to or removed from the positioning device as desired.

The positioning device may, for instance, be developed as robot arm or, more preferably, as positioning device comprising components of movement in two directions of travel in a plane and a third direction of travel vertical thereto such as a beam translation system. In the latter case, the pipetting module preferably is detachably fixed to a transfer head which is moveable towards and away from the plane. Detachably fixed in this context means that the pipetting module can be fixed to and detached from the positioning device without giving up the unity of the module. Preferably the pipetting module can be fixed to the positioning device and detached from it without disassembling or dismantling the pipetting module. This can be achieved by e.g. fixing the pipetting module with screws to the positioning device. It has to be understood that the pipetting module comprises the components as described further below herein.

The pipetting device according to an embodiment of the invention may further include a controller for controlling of pipetting operations. The controller may, e.g., be embodied as a programmable logic controller running a machine-readable program provided with instructions to perform operations in accordance with a predetermined process operation plan for pipetting of fluids.

Due to the modular construction of the at least one pipetting module enabling each of the pipetting modules to be fixed to and removed from the positioning device, respectively, the pipetting device of the present invention can be readily adapted to various needs as desired. In that, as defective pipetting modules may be easily replaced, maintenance of the pipetting device in case of failures is considerably simplified resulting in reduced downtime and maintenance costs. Furthermore, since the pipetting modules can be made small and compact in design, dead volumes between pump(s) and pipetting tips can be made small which advantageously enables high-precision pipetting of fluids.

According to a preferred embodiment of the pipetting device, the pipetting module is provided with a pump connected to the pipetting tip by means of the pump conduit to thereby obtain a highly-integrated pipetting device.

According to another preferred embodiment of the pipetting device, the pump conduit of the at least one pipetting module is fluidically connected to a liquid system fluid reservoir to at least partly fill the pump conduit with liquid system fluid which can either be transported towards the liquid system fluid reservoir to aspirate fluids into the fluid sample conduit or transported towards the pipetting tip to dispense fluids from the fluid sample conduit, regularly with a gas bubble in-between the (non-pipetted) liquid system fluid and the (pipetted) fluid samples.

The use of a liquid system fluid advantageously allows for high-precision pipetting of fluids due to a reduced compressibility of the liquid system fluid and lower temperature-induced variations compared to the otherwise purely gaseous system fluid.

When using liquid system fluid, it is highly preferred to use a pump of the rotary displacement pump type such as a gearwheel pump for generating positive or negative pressure to be transferred to the pipetting tip. While being comparably low in weight, a gearwheel pump advantageously allows for a definite transport of the liquid system fluid thus enabling very precise pipetting of fluids. Furthermore, a gearwheel pump enables pipetting of a wide range of volumes, so that a same pump may be used for both pipetting of fluid samples and pipetting of (the much higher volumes of) wash fluids in order to wash the fluid sample conduit. Otherwise, a gearwheel pump may be integrated into the pipetting module. The use of a gearwheel pump thus advantageously enables the pipetting device to have a reduced complexity as, for instance, reflected by avoiding usage of various pumps and tubing and saving constructional space.

In case fluids aspirated into the fluid sample conduit contain microscopic (solid) particles such as magnetic beads, which, for example, are being used in various nucleic acids separation techniques, is has been shown that such particles are very likely to be mixed with the liquid system fluid and may even get into the pump to cause severe damage due to an increased abrasion especially in case of using gearwheel pumps.

In order to overcome such a problem, it is preferred to arrange the fluid sample conduit for receiving the fluid samples aspirated through the pipetting tip in at least approximately vertical orientation with respect to gravity so that the fluid sample conduit extends along the direction of fall. Hence, providing for a vertically oriented fluid sample conduit, the solid particles contained therein may advantageously be made to drop down by the pure action of gravity which advantageously avoids the particles to be mixed with the liquid system fluid.

In order to overcome the problem of solid particles entering the liquid system fluid and in particular entering the gearwheel pump it is preferred that fluids containing such particles are only aspirated into the fluid sample conduit of the pipetting module but not beyond. This means that in a pipetting process the process is controlled to aspirate a volume of a particle containing fluid which is smaller than the volume of the fluid sample conduit of the pipetting module. Specifically, in the case of a pump conduit having plural windings including linearly extending portions connected by curved portions, as above-detailed, the fluid is only aspirated into the linearly extending portion directly connected (i.e. adjacent) to the pipetting tip but not in the curved portion directly connected (i.e. adjacent) to this linearly extending portion.

In the pipetting device according to an embodiment of the invention, each pipetting module may further include one or more sensors, adapted for sensing of physical parameters, e.g. flow rate and liquid pressure in the fluid sample conduit, in particular, when pipetting operations are being performed, or for sensing of a distance between the pipetting tip and another object such as a work-surface. For instance in the case of a pump conduit having plural windings including linearly extending portions connected by curved portions, as above-detailed, the pipetting module may include a sensor for detecting a boundary between liquid and gas or between two types of liquid so as to avoid aspirating fluids beyond the fluid sample conduit.

According to yet another preferred embodiment of the pipetting device, the at least one pipetting module has a housing at least partly accommodating the pump conduit which allows for a quick fixing or removing, in particular replacing, of the pipetting module. In case of using liquid system fluid, it may be preferable that an outer conduit disposed outside the housing be exclusively filled with liquid system fluid. It may also be preferred to provide the housing with at least one connector selected from the group consisting of a fluidic connector and an electric connector enabling a highly-compact and flexible design of the pipetting module.

In yet another preferred embodiment of the invention, the pipetting device is being provided with a plurality of pipetting modules, each being detachably fixed to the automated positioning device. In that, the pipetting modules may be serially aligned with respect to each other, wherein a distance in-between adjacent pipetting tips is being adapted to correspond to a distance in-between adjacent cavities used for pipetting of fluid samples. Hence, the pipetting device may advantageously be used for pipetting of fluids contained in equally-distanced cavities, such as wells of multi-well plates.

According to another embodiment of the invention, a modular pipetting unit for detachably attaching to an automated positioning device of a pipetting device for pipetting of fluid samples is provided. The modular pipetting unit includes at least one pipetting tip for pipetting fluid samples and a pump conduit for transferring a negative or positive pressure to the pipetting tip, wherein the pipetting tip and at least a portion of the pump conduit adjoining the pipetting tip mutually define a fluid sample conduit for receiving the fluid samples.

According to another embodiment of the invention, a method for pipetting of fluid samples using a pipetting device is provided. The pipetting device for use with the method comprises at least one (e.g. modular) pipetting unit including a pipetting tip for pipetting of fluid samples and a pump conduit for transferring a negative or positive pressure to the pipetting tip, wherein the pipetting tip and at least a portion of the pump conduit adjoining the pipetting tip mutually define a fluid sample conduit for receiving the fluid samples. In the method of the invention, pipetting of fluid samples is performed in such a manner that a pipetted volume of a fluid sample that contains solid particles is smaller than a volume of the fluid sample conduit. More preferably, each volume of pipetted fluid sample is smaller than a volume of the fluid sample conduit. Further in a preferred method of the invention the pipetting processes are controlled so that sample fluid does not leave the pipetting module in direction of the system fluid reservoir.

According to another embodiment of the invention, a pipetting system is provided. The pipetting system comprises at least one pipetting unit including a pipetting tip for pipetting of fluid samples and a pump conduit for transferring a negative or positive pressure to the pipetting tip, wherein the pipetting tip and at least a portion of the pump conduit adjoining the pipetting tip mutually define a fluid sample conduit for receiving the fluid samples. The fluid sample conduit most preferably is at least approximately vertically aligned. It further comprises an automated positioning device for positioning of the at least one pipetting unit and a controller for controlling of pipetting of fluid samples. In the system of the invention, the controller is configured to control pipetting of fluid samples in such a manner that each pipetted volume of the fluid samples is smaller than a volume of the fluid sample conduit.

According to a preferred embodiment of the system, the pipetting unit is a modular pipetting unit (pipetting module) being detachably fixed to the automated positioning device. In that case it may be highly preferred to have a pump accommodated in the modular pipetting unit which is being connected to the pipetting tip by means of the pump conduit.

The above embodiments of the present invention will now be described in greater detail below with reference to the accompanying drawings, where like designations denote like or similar elements.

Figure 1:
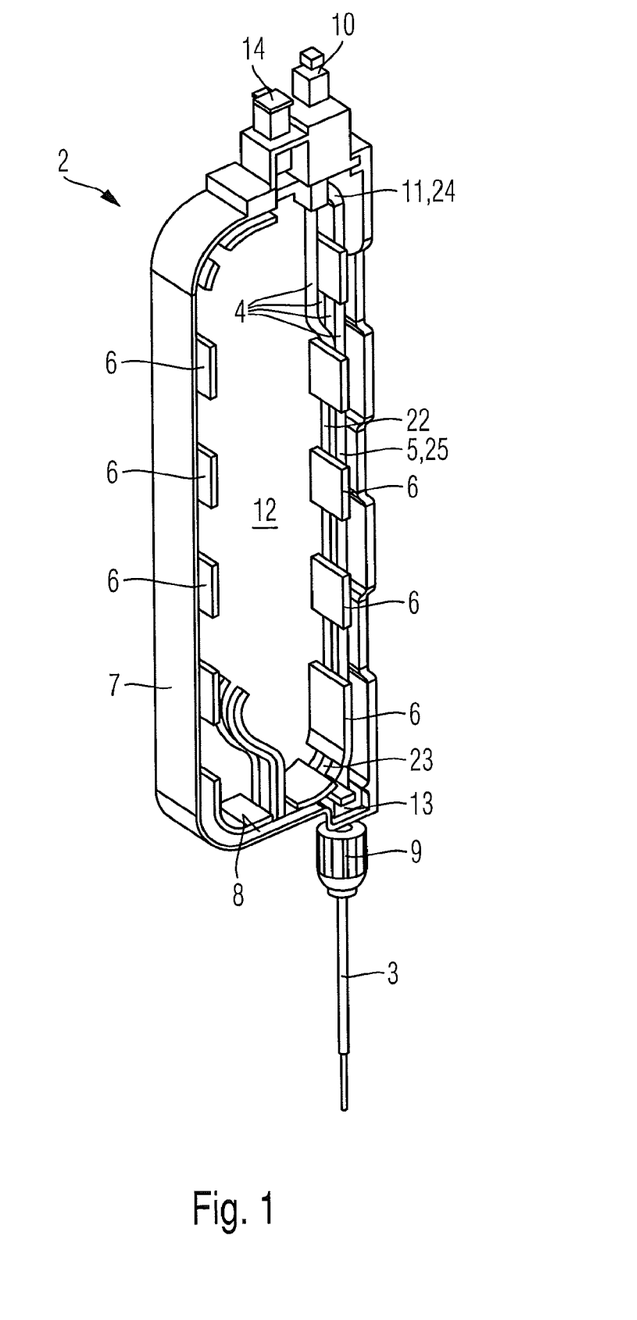
FIG. 1 is a schematic perspective view of an exemplary embodiment of a pipetting module according to the invention.

Referring to FIG. 1, an exemplary embodiment of the modular pipetting unit (pipetting module) according to the invention is explained. Accordingly, a pipetting module 2 (modular pipetting unit) includes a re-usable pipetting tip 3 (needle) for pipetting of fluid samples which is fixed to an elongated hollow cartridge 7 (housing) by means of a threaded connection. The threaded connection is comprised of a threaded pin screwed into a threaded hole of the cartridge 7 (not further detailed in FIG. 1). A corrugated outer surface 9 at the cartridge 7-sided end of the pipetting tip 3 facilitates turning of the pipetting tip 3 for screwing or unscrewing with cartridge 7. The pipetting tip 3 may thus be readily fixed or removed and replaced by another pipetting tip 3 as desired.

The pipetting tip 3 which is made of metallic material (e.g. steel) is fluidically connected to a plastic-made flexible pump conduit 4 accommodated in a cavity 12 of the cartridge 7 for transferring a pump-generated negative or positive pressure to the pipetting tip 3. The cavity 12 of the cartridge 7 is provided with a plurality of guiding faces 6 arranged along an inner wall 8 of cartridge 7 for guiding the pump conduit 4. Supported by the guiding faces 6, the pump conduit 4 winds three and a half times along the inner wall 8 of housing 7 to be finally connected with a fluidic connector 10.

Due to a nearly rectangular (parallel-epipedic) shape of the cavity 12, the pump conduit 4 has longer (linearly extending) conduit portions 22 in a first direction and shorter (linearly extending) conduit portions 23 in a second direction vertically aligned to the first direction, which are connected by curved conduit portions 24. When orienting the elongated cartridge 7 in vertical direction with respect to gravity, the longer conduit portions 22 extend in vertical direction.

Specifically, the pump conduit 4 includes a first longer portion 5 which, being linearly aligned with the pipetting tip 3, extends from the pipetting tip 3 to the beginning of the first curved conduit portion 11 of the pump conduit 4. The first longer portion 5 of the pump conduit 4 and the pipetting tip 3 may mutually define a fluid sample conduit 25 for receiving fluid samples aspirated through the pipetting tip 3. When vertically orienting the elongated cartridge 7 (i.e. vertically orienting the pipetting tip 3), the fluid sample conduit 25 extends in the direction of fall.

When using liquid system fluid, the vertically oriented fluid sample conduit 25 causes microscopic (solid) particles such as magnetic beads contained in fluid samples to drop down by the pure action of gravity which advantageously avoids diffusing the particles into the liquid system fluid. For this reason fluid samples containing microscopic particles preferably are only aspirated into this vertically oriented fluid sample conduit 25 but not beyond, i.e., such fluid samples are not aspirated into the first curved conduit portion 11. Otherwise, fluid samples free of microscopic particles can also be aspirated beyond the first lower portion 5 of the pump conduit 4. In the latter case, one or more longer conduit portions 22, one or more shorter conduit portions 23, one or more curved conduit portions 24 and the pipetting tip 3 may mutually define a fluid sample conduit.

A pipetting unit with such an internal fluid sample conduit 25 has a significant advantage. When pipetting is controlled in a way that other fluids than system fluid are only aspirated into this fluid sample conduit 25 this will be the only place where contamination can occur. In practice substances as e.g. proteins contained in sample fluids are adsorbed on the inner walls of the conduit. During subsequent pipetting processes such adsorbed substances are partially desorbed and contaminate dispensed fluids. In practice contaminated tubings have to be replaced after some month, the time very much depending on the type of sample fluids and intensity of usage. Replacement of the tubings can be quite cumbersome and often needs a service technician. Due to the modular pipetting unit of the present invention this service action can be simplified very much because the only item to be exchanged is the detachable pipetting unit which incorporates the tubing to be exchanged.

Further modular pipetting units are advantageous which have at least one winding of the pump conduit inside the pipetting unit. By this the volume capacity of the pipetting unit is increased and pipetting processes are not so restricted by the requirement that fluid samples are only aspirated into the pipetting unit but not beyond.

Having a fluid conduit inside the housing of the modular pipetting unit further has the advantage that the conduits are protected against mechanical stress and ultraviolet radiation. Further a metal housing provides protection against electromagnetic radiation so that detections of e.g. phase boundaries, liquid level detection are not disturbed.

In order to enable pipetting of sufficiently large volumes of fluid samples, the first longer portion 5 of the pump conduit 4 preferably has a length of more than 5 cm and may, e.g., have a length in a range of from 5 to 25 cm to achieve sufficiently strong inhibition of particle diffusion. Furthermore, the first longer portion 5 of the pump conduit 4 preferably has a diameter of less than 3 mm.

The pipetting module 2 further includes a sensor arrangement 13 comprising plural sensors electrically connected to a controller (not illustrated) for controlling of pipetting operations. The pipetting module 2 is provided with an electric connector 14 to be connected with electric lines for connecting the pipetting module 2 with the controller. Sensors of the sensor arrangement 13 are being adapted for sensing of physical parameters, in particular during pipetting of fluids, such as fluid flow rate and fluid pressure in the fluid sample conduit 25, or a distance between the pipetting tip 3 and another object such as a work-surface. Further such sensor can be a sensor for detecting a boundary between liquid and gas or between two types of liquid. This enables to either control and/or monitor pipetting processes based on the sensor signals. E.g. it can be avoided to aspirate fluid samples beyond the sample fluid conduit by monitoring close to the upper end of the sample fluid conduit that no gas/liquid or liquid/liquid boundary passes by during an aspiration. Suitable sensors can be e.g. optical sensors or inductive sensors which detect changes of optical properties or of inductance at phase boundaries.

In FIG. 1, the cartridge 7 is shown without side walls for the purpose of illustration only. Stated more particularly, the cartridge 7 is a closed housing aside from the screwed hole for fixing the pipetting tip 3 and the fluidic connector 10.

Figure 2:
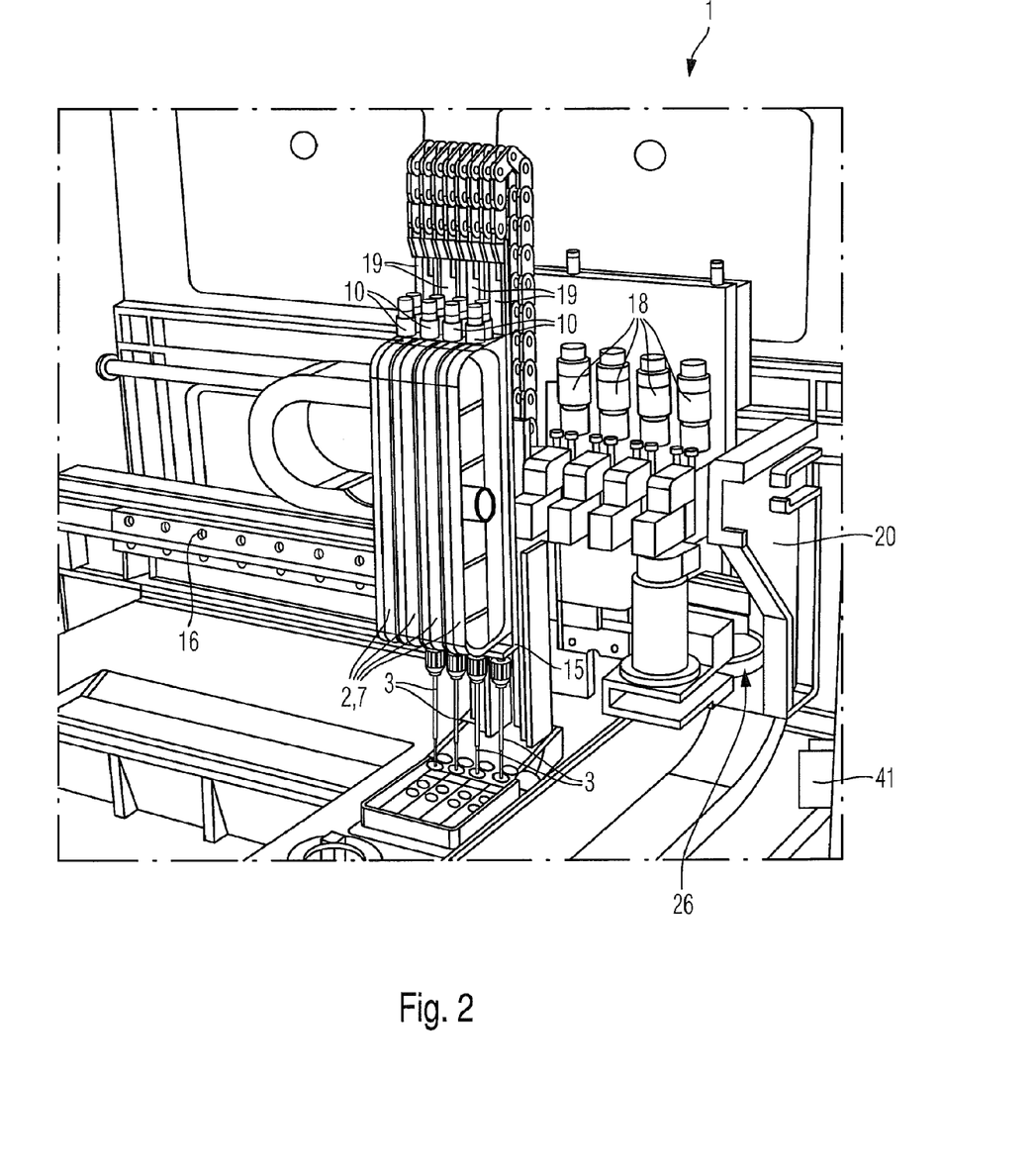
FIG. 2 is a schematic perspective view of an exemplary embodiment of a pipetting device of the invention including plural pipetting modules as illustrated in FIG. 1.

Referring to FIG. 2, an exemplary embodiment of the pipetting device 1 according to the invention is explained. The pipetting device 1 includes a plurality of pipetting modules 2 as illustrated in FIG. 1. Accordingly, each of the pipetting modules 2 includes a pipetting tip 3 which is fixed to cartridge 7 and connected to the pump conduit 4 accommodated therein. While a number of four pipetting modules 2 are illustrated in FIG. 2, it, however, is to be understood that more or less pipetting modules 2 can be used in accordance with specific demands for the pipetting of fluid samples.

The pipetting device 1 includes an automated positioning device 26 which can be used to transfer the pipetting tips 3 with respect to cavities containing the fluid samples to be transferred. Each pipetting module 2 is detachably mounted to a transfer head 15, which can be slidably moved in vertical direction along vertically extending vertical guiding rails 19, e.g., by means of a spindle drive. The vertical guiding rails 19 for guiding the transfer head 15 are fixed to a sliding carriage 20 which can be moved in two directions of travel in a horizontal plane using a two-rail translation system comprising two rails arranged in orthogonal relationship with respect to each other for moving the transfer head 15. In FIG. 2, one horizontal guiding rail 16 is illustrated. Since such positioning system is well-known to those of skill in the art, it is not further detailed herein.

Each pipetting module 2 is vertically oriented with respect to gravity which results in vertically oriented fluid sample conduits 25 for accommodating fluid samples aspired through the pipetting tips 3, so that microscopic particles contained in the fluid samples are caused to drop down by the action of gravity.

In the pipetting device 1, the fluidic connector 10 of each of the pipetting modules 2 is fluidically connected to a micro-gearwheel pump 18 by the pump conduit 4, which is guided by a separate metallic guiding chain 17 comprised of plural chain links 21 to mechanically protect the pump conduit 4. Each gearwheel pump 18 is fixed to the sliding carriage 20 and thus moves together with the sliding carriage 20 in a horizontal plane. Alternatively, the micro-gearwheel pumps 18 might be fixed to the transfer head 15. Each gearwheel pump 18 is fluidically connected to a system fluid reservoir 32 by means of a reservoir tubing 29 (schematically illustrated in FIG. 4).

As illustrated in FIG. 2, in the pipetting device 1, the pipetting modules 2 are serially aligned with respect to each other, wherein a distance in-between adjacent pipetting tips 3 is chosen to correspond to a distance in-between adjacent cavities of a plurality of equally-distanced cavities containing the fluid samples to be transferred. The pipetting device 1 of FIG. 2 may thus advantageously be used for pipetting of fluid samples contained in equally-distanced cavities, such as multi-well plates.

Figure 3:
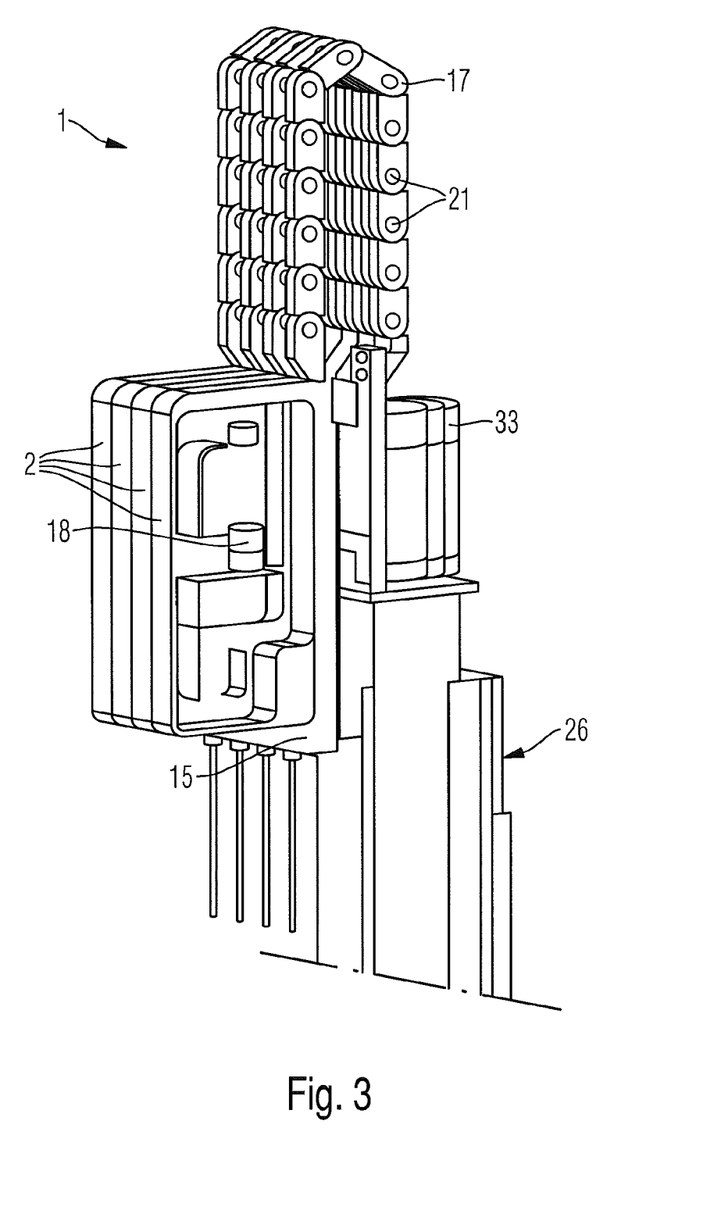
FIG. 3 is a schematic perspective view of a variant of the pipetting device of FIG. 2, wherein each pipetting module accommodates a micro-gearwheel pump.

Reference is now made to FIG. 3 illustrating a variant of the pipetting device of FIG. 2. In order to avoid unnecessary repetitions only differences with respect to FIG. 2 are explained and otherwise reference is made to explanations made in connection with FIG. 2. In the pipetting device of FIG. 3, each pipetting module 2 accommodates a micro-gearwheel pump 18 which is fluidically connected to the pump conduit 4 for generating a positive or negative pressure in the pipetting tips 3. Each gearwheel pump 18 accommodated in the cartridge 7 is fluidically connected to a system fluid reservoir 32 by means of a reservoir tubing 29 (schematically illustrated in FIG. 4). In that, the reservoir tubing 29 of each of the pipetting modules 2 is at least partly guided by a separate metallic guiding chain 17 to provide for mechanical protection. Said guiding chain 17 having a number of rigid chain elements which are fixed to each other in a way which allows relative movement in one direction. The chain elements each having a channel. The channels of the chain elements being aligned in a way to provide a channel in which the reservoir tubing 29 is housed and by that sheltered as well as able to follow the up- and down movements of the respective pipetting module.

In FIG. 3, a DC electric motor 33 for vertically driving the transfer head 15 is depicted. Each pipetting module 2 of the pipetting device 1 of FIG. 3 having an integrated micro-gearwheel pump 18 thus advantageously allows for a reduced complexity of the pipetting device 1 to thereby save constructional space and costs and facilitate maintenance operations.

Figure 4:
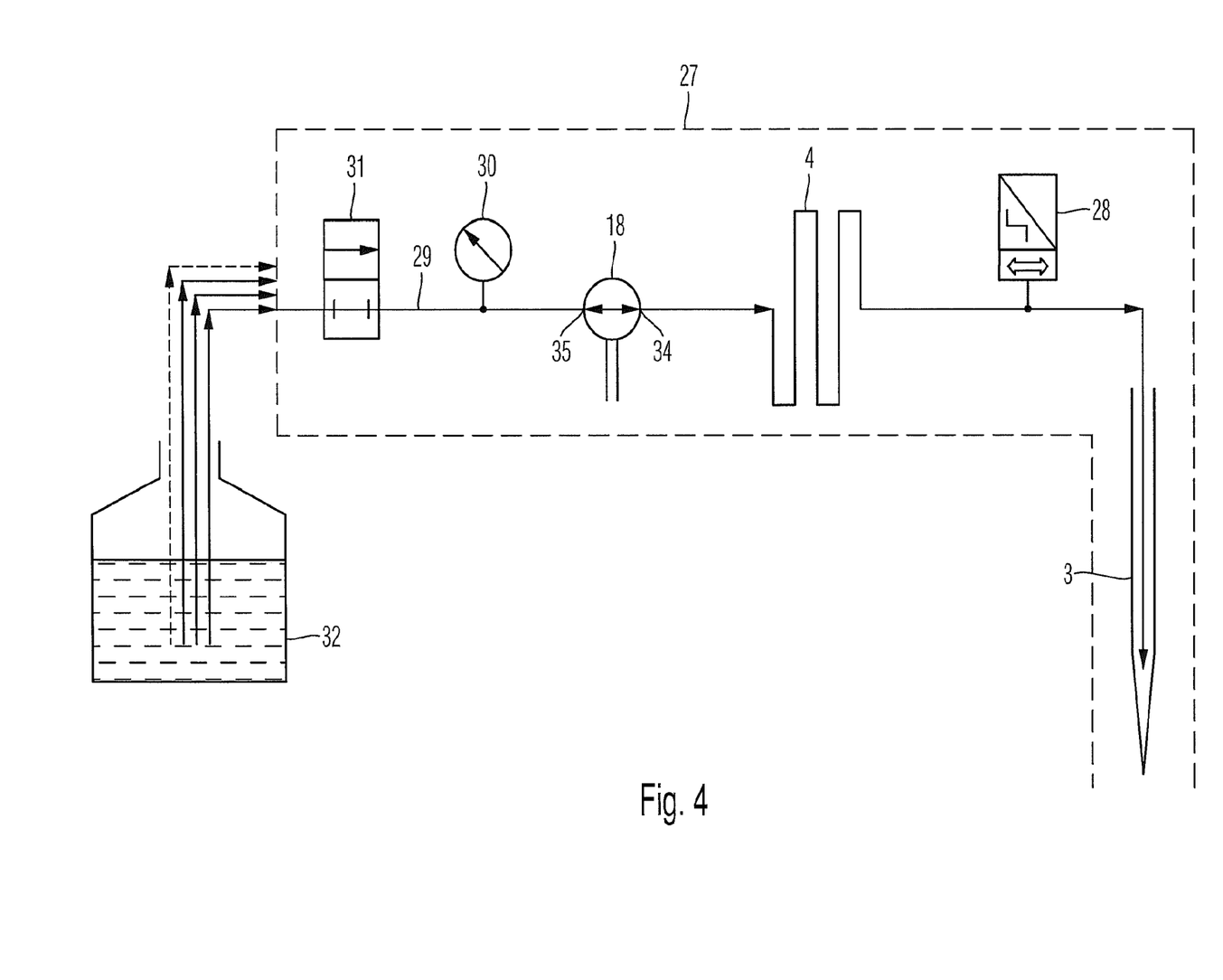
FIG. 4 is a schematic diagram of a pipetting channel of the pipetting device of FIG. 2 or 3 connected to a liquid system fluid reservoir.
Figure 5A:
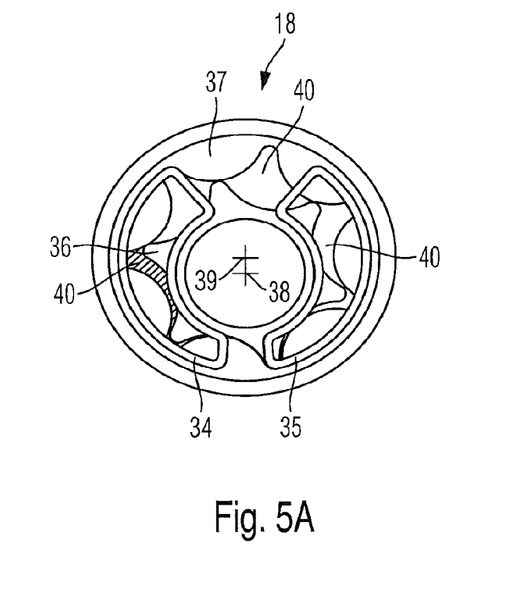
FIGS. 5A-5D are schematic cross-sectional views illustrating operation of a micro-gearwheel pump.
Figure 5B:
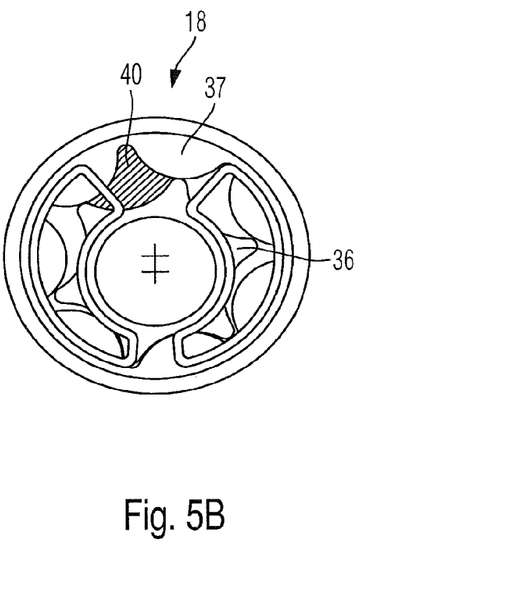
Figure 5C:
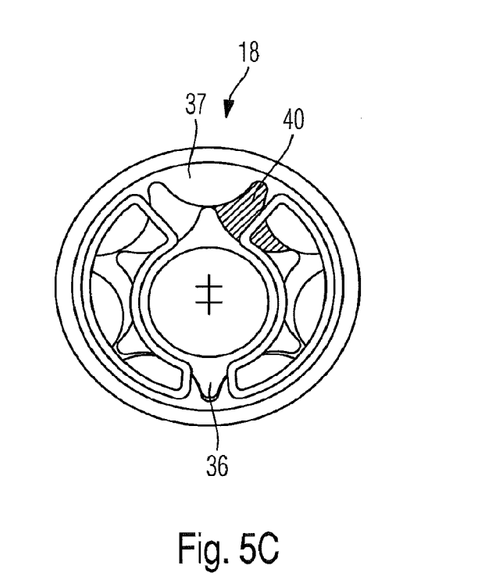
Figure 5D:
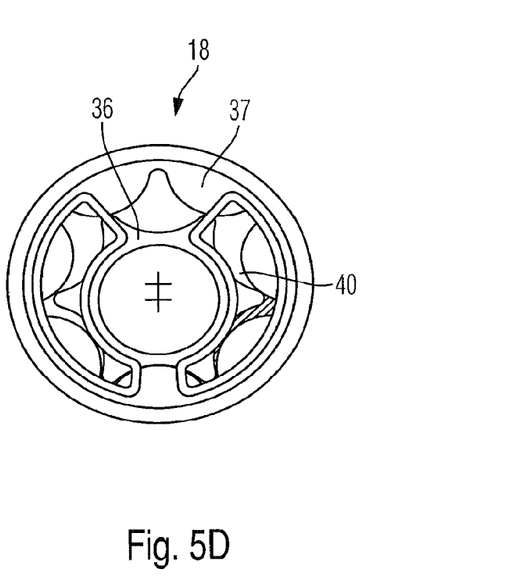

Reference is now made to FIG. 4 illustrating a schematic diagram of a pipetting channel 27 including a pipetting module 2 of the pipetting device 1 of FIG. 2 or FIG. 3 used for pipetting of fluid samples. The pipetting channel 27 is a functional entity for pipetting of fluids including an individual pipetting module 2. Due to four pipetting modules 2, the pipetting device 1 has a number of four identical pipetting channels 27, each of which including an individual pipetting module 2.

Accordingly, an individual pipetting channel 27 of the pipetting device 1 including an individual pipetting module 2 comprises:
the pipetting tip 3 of the pipetting module 2;
the pump conduit 4 connecting the pipetting tip 3 with a first inlet/outlet port 34 of the gearwheel pump 18; and
a reservoir tubing 29 connecting a second inlet/outlet port 35 of the gearwheel pump 18 with a system fluid reservoir 32.

The pump conduit 4 is provided with an optical flow sensor 28 used for sensing of fluid flows in the fluid sample conduit 25 which is part of the sensor arrangement 13. Further, the reservoir tubing 29 passes through system fluid valve 31, adapted for opening/closing reservoir tubing 29, and is provided with a pressure sensor 30 for sensing of system fluid pressure in reservoir tubing 29.

The gearwheel pump 18 for generating a positive or negative pressure in the pipetting tip 3 of each of the pipetting channels 27 is connected to the liquid system fluid reservoir 32 for at least partly filling the reservoir tubing 29 or for (completely) filling the reservoir tubing 29 and at least partly filling the pump conduit 4 (at least except for the fluid sample conduit 25) of the pipetting channel 27 with liquid system fluid. In case the micro-gearwheel pump 18 is located outside the cartridge 7, it can be preferred to exclusively fill the reservoir tubing 29 and those parts of the pump conduits 4 which are located outside the cartridge 7 with liquid system fluid.

In case the gearwheel pump 18 is accommodated in the cavity 12 of the cartridge 7 of the pipetting module 2 to which it belongs, each of the pipetting channels 27 is a structural entity as identified by the pipetting module 2. In other words, each of the pipetting modules 2 may include all components of a pipetting channel 27 as illustrated in FIG. 3.

Reference is now made to FIGS. 5A-5D illustrating cross-sectional views of the micro-gearwheel pump 18 of the pipetting device 1 of FIG. 2 and FIG. 3. The micro-gearwheel pump 18 includes an inner rotor (externally toothed inner gearwheel) 36 turning around an inner rotor rotation axis 38 and an outer rotor (internally toothed outer gearwheel) 37 turning around an outer rotor rotation axis 39, with both axes 38, 39 being offset with respect to each other. The inner and outer rotors 36, 37 are in meshing engagement to thereby circumferentially form pressure chambers 40 cyclically changing their sizes and positions when rotating the inner rotor 36 with respect to the outer rotor 37. The pressure chambers are connected to the first and second inlet/outlet ports 34, 35 to generate low-pulsation flows of liquid system fluid between the ports when increasing the pressure chambers 40 at the aspirating port and decreasing the pressure chambers 40 at the dispensing port. The direction of flow can be reversed in changing the driving direction of the micro-gearwheel pump 18.

In FIGS. 5A-5D, four consecutive positions of the inner rotor 36 with respect to the outer rotor 37 are depicted illustrating transport of fluid from the first inlet/outlet port 34 (aspirating port) to the second inlet/outlet port 35 (dispensing port) in turning the inner rotor 36 in clockwise direction.

Accordingly, generating a liquid system fluid flow directed to the system fluid reservoir 32 (system fluid reservoir 32 is connected to the dispensing port of the micro-gearwheel pump 18) generates a negative pressure in the pipetting tip 3 to thereby aspire fluid into the fluid sample conduit 25. On the other hand, generating a liquid system fluid flow directed to the pipetting tip 3 (pipetting tip 3 is connected to the dispensing port of the micro-gearwheel pump 18) generates a positive pressure in the pipetting tip 3 to thereby dispense fluid contained in the fluid sample conduit 25.

The system fluid valve 31 is operatively coupled to the micro-gearwheel 18 and is opened when a pumping operation of the micro-gearwheel pump 18 is performed to enable liquid system fluid flow through the reservoir tubing 29 and is closed when the micro-gearwheel pump 18 is not operated to close the reservoir tubing 29. Pressure sensor 30 is used for sensing of system fluid pressure in reservoir tubing 29.

The micro-gearwheel pump 18 may, e.g., be used for pipetting of fluid sample volumes in a range of from 10 μl to 1500 μl. Moreover, it may, e.g., be used for pipetting of fluid samples having flow rates in a range of from 1200 μl/sec to 72 ml/sec. Based upon such a wide range of flow rates, the micro-gearwheel pump 18 may also be used for washing the pipetting tips 3, for instance, in dispensing liquid system fluid through the pipetting tips 3.

While, in above embodiments, the pipetting modules 2 have been shown each to be connected to a separate micro-gearwheel pump 18, in particular in case of locating the micro-gearwheel pump 18 outside the pipetting module 2, it may be preferable to connect the pipetting modules 2 to a single common gearwheel pump 18.

While the pipetting modules 2 have been shown to be mounted to a same transfer head 15 in above embodiment, it may be preferable to mount each of the pipetting modules 2 to a separate transfer head 15 to independently move the pipetting tips 3.

The pipetting device 1 further includes a controller 41 for controlling of pipetting of fluids of each of the pipetting channels 27. In that, the controller is being configured to control pipetting of each of the pipetting channels 27 in such a way that each pipetted volume of fluids is smaller than a volume of the fluid sample conduit 25 of the pipetting module 2 concerned.

Accordingly, by the above discussion a pipetting device 1 has been disclosed which comprises at least one modular pipetting unit 2 including a pipetting tip 3 for pipetting of fluid samples and a pump conduit 4 for transferring a negative or positive pressure to the pipetting tip 3, wherein the pipetting tip 3 and at least a portion 5 of the pump conduit 4 adjoining the pipetting tip 3 mutually define a fluid sample conduit 25 for receiving the fluid samples, and wherein the modular pipetting unit 2 being detachably attached to an automated positioning device 26 for positioning the modular pipetting unit 2.

In another embodiment, the modular pipetting unit 2 has an integrated pump 18 connected to the pipetting tip 3 by means of the pump conduit 4.

In another embodiment, the pump is a pump of the rotary displacement pump type such as a gearwheel pump 18.

In another embodiment, the pump conduit 4 is being at least partly filled with a liquid system fluid.

In another embodiment, the fluid sample conduit 25 has an at least approximate vertical orientation with respect to gravity.

In another embodiment, the modular pipetting unit 2 comprises at least one sensor 13 adapted for sensing of physical parameters.

In another embodiment, the modular pipetting unit 2 includes a housing 7 at least partly accommodating the pump conduit 4.

In another embodiment, the housing 7 is provided with at least one connector selected from the group consisting of a fluidic connector 10 and an electric connector 14.

In another embodiment, the automated positioning device 26 comprises components of movement in two directions of travel in a plane and a third direction of travel vertical thereto, wherein the modular pipetting unit 2 is detachably attached to a transfer head 15 moveable along the third direction.

In another embodiment, the pipetting device 1 comprises a plurality of modular pipetting units 2 having a plurality of equally-distanced pipetting tips 3, wherein a distance in-between adjacent pipetting tips 3 corresponds to a distance in-between adjacent cavities used for pipetting of the fluid samples.

In another embodiment, a modular pipetting unit 2 comprises at least one pipetting tip 3 for pipetting of fluid samples and a pump conduit 4 for transferring a negative or positive pressure to the pipetting tip 3, wherein the pipetting tip 3 and at least a portion 5 of the pump conduit 4 adjoining the pipetting tip 3 mutually define a fluid sample conduit 25 for accommodating the fluid samples.

In still another embodiment, a method for pipetting of fluid samples has been disclosed and comprises using a pipetting device 1 comprising at least one pipetting unit 2 provided with a pipetting tip 3 for pipetting of fluid samples and a pump conduit 4 for transferring a negative or positive pressure to the pipetting tip 3, wherein the pipetting tip 3 and at least a portion 5 of the pump conduit adjoining the pipetting tip mutually define a fluid sample conduit 25 for receiving the fluid samples, wherein pipetting of the fluid samples is performed in such a way that a pipetted fluid sample volume is smaller than a volume of the fluid sample conduit 25.

In yet another embodiment, a pipetting system has been disclosed and comprises at least one pipetting unit 2 which includes a pipetting tip 3 for pipetting fluid samples and a pump conduit 4 for transferring a negative or positive pressure to the pipetting tip 3, wherein the pipetting tip 3 and at least a portion 5 of the pump conduit adjoining the pipetting tip 3 mutually define a fluid sample conduit 25 for receiving the fluid samples; an automated positioning device 26 for positioning of the at least one pipetting unit 2; and a controller 41 for controlling of pipetting of the fluid samples, configured to control pipetting of fluids such that each pipetted volume of the fluid samples is smaller than a volume of the fluid sample conduit.

In another embodiment and in the pipetting system, the pipetting unit 2 is a modular pipetting unit being detachably attached to the automated positioning device.

In another embodiment and in the pipetting system, the modular pipetting unit 2 accommodates a pump 18 connected to the pipetting tip 3 by means of the pump conduit 4.

Obviously many modifications and variations of the present invention are possible in light of the above description. It is therefore to be understood, that within the scope of appended claims, the invention may be practiced otherwise than as specifically devised.

What is claimed is:

1. A pipetting device for an automated positioning device, comprising:
    at least one modular pipetting unit which includes a pipetting tip for pipetting of fluid samples;
        a pump conduit tot transferring a negative or positive pressure to said pipetting-tip,
        a hollow housing comprising an inner wall surrounding a cavity and a plurality of guiding faces arranged along the inner wall guiding the pump conduit, said pump conduit comprising a first vertical conduit portion extending in the direction of gravity, a second horizontal conduit portion, and a first curved conduit portion connecting said first vertical conduit portion to said second horizontal conduit portion, said first vertical conduit portion being longer than the second horizontal conduit portion;
    wherein said pipetting tip and at least a portion of said pump conduit adjoining said pipetting tip mutually define a fluid sample conduit for receiving said fluid samples, and
    wherein said modular pipetting unit is detachably attachable to the automated positioning device which positions said modular pipetting unit.

2. The pipetting device according to claim 1, wherein said modular pipetting unit has an integrated pump connected to said pipetting tip by means of said pump conduit.

3. The pipetting device according to claim 2, wherein said pump is a pump of the rotary displacement pump type such as a gearwheel pump.

4. The pipetting device according to claim 1, wherein said fluid sample conduit and pipetting tip have an at least approximate vertical orientation with respect to gravity.

5. The pipetting device according to claim 1, wherein said modular pipetting unit comprises at least one sensor for sensing of physical parameters selected from the group consisting of flow rate, liquid pressure, and distance.

6. The pipetting device according to claim 1, wherein said housing is provided with at least one connector selected from the group consisting of a fluidic connector and an electric connector.

7. The pipetting device according to claim 1, comprising a plurality of modular pipetting units having a plurality of equally-distanced pipetting tips.

8. A modular pipetting unit comprising:
    at least one pipetting tip for pipetting of fluid samples;
    a pump conduit tot transferring a negative or positive pressure to said at least one pipetting tip; and
    a hollow housing comprising an inner wall surrounding a cavity and a plurality of guiding faces arranged along the inner wall guiding the pump conduit, said pump conduit comprising a first vertical conduit portion extending in the direction of gravity, a second horizontal conduit portion, and a first curved conduit portion connecting said first vertical conduit portion to said second horizontal conduit portion, said first vertical conduit portion being longer than the second horizontal conduit portion;
    wherein said at least one pipetting tip and at least a portion of said pump conduit adjoining said at least one pipetting tip mutually define a fluid sample conduit for accommodating said fluid samples.

9. A pipetting system, comprising:
    at least one pipetting unit which includes a pipetting tip for pipetting fluid samples and a pump conduit for transferring a negative or positive pressure to said pipetting tip, the at least one pipetting unit comprising a hollow housing comprising an inner wall surrounding a cavity and a plurality of guiding faces arranged along the inner wall guiding the pump conduit, said pump conduit comprising a first vertical conduit portion extending in the direction of gravity, a second horizontal conduit portion, and a first curved conduit portion connecting said first vertical conduit portion to said second horizontal conduit portion, said first vertical conduit portion being longer than the second horizontal conduit portion, wherein said pipetting tip and at least a portion of said pump conduit adjoining said pipetting tip mutually define a fluid sample conduit for receiving said fluid samples;
    an automated positioning device for positioning of the at least one pipetting unit; and
    a controller for controlling pipetting of said fluid samples such that each pipetted volume of the fluid samples is smaller than a volume of said fluid sample conduit.

10. The pipetting system according to claim 9, wherein said at least one pipetting unit is a modular pipetting unit being detachably attached to said automated positioning device.

11. The pipetting system according to claim 10, wherein said modular pipetting unit comprises a pump connected to said pipetting tip by said pump conduit.

12. The pipetting system according to claim 9, comprises a liquid system fluid reservoir, wherein said pump conduit is fluidically connected to the liquid system fluid reservoir containing a liquid system fluid and the pump conduit is filled with an amount of the liquid system fluid.

13. The pipetting system according to claim 9, wherein said fluid sample conduit and pipetting tip have an at least approximate vertical orientation with respect to gravity.

14. The pipetting system according to claim 9, wherein said pipetting unit comprises at least one sensor for sensing of physical parameters selected from the group consisting of flow rate, liquid pressure, and distance.

15. The pipetting system according to claim 9, wherein said housing is provided with at least one connector selected from the group consisting of a fluidic connector and an electric connector.

\* \* \* \* \*